United States Patent [19]

Suzuki et al.

[11] Patent Number: 5,523,276
[45] Date of Patent: Jun. 4, 1996

[54] STABLE HERBICIDAL COMBINATION COMPOSITIONS

[75] Inventors: Munehiro Suzuki, Aichi; Masaomi Kimpara, Shizuoka, both of Japan

[73] Assignee: American Cyanamid Company, Madison

[21] Appl. No.: 454,804

[22] Filed: May 31, 1995

Related U.S. Application Data

[63] Continuation of Ser. No. 439,582, May 23, 1995, abandoned, which is a continuation-in-part of Ser. No. 107,410, Aug. 16, 1993, abandoned.

[51] Int. Cl.$^6$ .................................. A01N 43/54
[52] U.S. Cl. .................. 504/136; 504/143; 504/148; 504/149; 71/DIG. 1
[58] Field of Search ............................ 504/136, 143, 504/148, 149

[56] References Cited

U.S. PATENT DOCUMENTS 4,222,065  11/1986  Van Gemert ........................ 544/321
5,009,699   4/1991  Brady et al. ........................ 544/321
5,280,007   1/1994  Kawai ................................. 504/105

OTHER PUBLICATIONS

The Pesticide Manual, 9th Ed., 1991, pp. 13, 14, 106, 338, 594, 595, 656, 657, 699, 815, 851 and 852.

Carplex Shionogi, Amorphous Hydrous Silicon Dioxide (SiO2.m H2O), Shionogi & Co., Ltd., Japan, 1993.

*Primary Examiner*—Richard L. Raymond
*Assistant Examiner*—B. Bembenick
*Attorney, Agent, or Firm*—Peggy A. Climenson

[57] ABSTRACT

There is provided a stable herbicidal composition comprising 1-{ [o-(cyclopropylcarbonyl)-phenyl] sulfamoyl} -3-(4, 6-dimethoxy-2-pyrimidinyl)urea in combination with one or more low-melting or liquid herbicides and alkaline white carbon.

24 Claims, No Drawings

STABLE HERBICIDAL COMBINATION COMPOSITIONS

This is a continuation of application Ser. No. 08/439,582 filed on May 23, 1995, (abandoned) which is a continuation-in-part of application Ser. No. 08/107,410 filed on Aug. 16, 1993 (abandoned).

BACKGROUND OF THE INVENTION

In order to control a wide variety of troublesome broadleaf and grass weed species in the presence of cereal crops, especially in rice culture (upland and paddy), a combination application of one or more herbicides is generally required. The compound, 1-{ [o-(cyclopropylcarbonyl)phenyl]sulfamoyl}-3-(4,6 -dimethoxy-2-pyrimidinyl)urea is a crop-selective herbicide which is highly effective in controlling broadleaf weeds and sedges and is described in U.S. Pat. No. 5,009,699. In present day agronomic practice a number of effective grass herbicides are available which are selective in cereal crops such as dinitroaniline herbicides, thiocarbamate herbicides and chloroacetamide herbicides. However, many of these herbicides are liquids or low-melting solids and when one or more are used in combination with the abovesaid sulfamoyl urea to achieve broad spectrum weed control in the presence of cereal crops, the sulfamoyl urea compound may become unstable with the passage of time and lose its efficacious properties.

It is, therefore, an object of this invention to provide a stable combination herbicide composition for the control of noxious grass and broadleaf plant species and sedges which plague cereal crops, especially upland rice crops and paddy rice fields.

SUMMARY OF THE INVENTION

This invention relates to a stable herbicidal composition which comprises 1-{[o-cyclopropylcarbonyl)phenyl] sulfamoyl}-3-(4,6-dimethoxy-2-pyrimidinyl)urea in combination with one or more low-melting of liquid herbicides and alkaline white carbon. Advantageously, the herbicidal combination composition of the invention may be used to provide excellent control of a broad spectrum of grass and broadleaf weeds and sedge in the presence of growing, seeded or transplanted cereal crop plants, even after prolonged storage.

DESCRIPTION OF THE INVENTION

Cereal grains such as rice, wheat, barley, oats and rye are considered to be among the most important food crops. For example, rice is the major dietary component for greater than one-third of the world's population. Grain production, to be efficient, often requires the use of two or more herbicides in a combination application to control the full spectrum of noxious plant species, for example, those which plague rice paddy fields and upland rice crops.

The compound 1-{[o-(cyclopropylcarbonyl)phenyl] sulfamoyl}-3-(4,6-dimethoxy-2-pyrimidinyl)urea, hereinafter referred to as the sulfamoyl urea compound, is a potent crop-selective herbicide which may be used in very low quantities and is especially effective for the control of sedges and broadleaf weed species in the presence of cereal crops such as barley, wheat, oats, and rye, as well as rice. This sulfamoyl urea compound is described in U.S. Pat. No. 5,009,699. Readily available, low-melting or liquid, herbicidal agents which are chiefly used for weed control in cereal crop production and are especially effective for control of annual grass weeds are: dinitroaniline herbicides such as pendimethalin, trifluralin and the like; thiocarbamate herbicides such as esprocarb, thiobencarb, molinate and the like and chloroacetamide herbicides such as butachlor, pretilachlor, metolachlor, alachlor and the like.

A combination of the sulfamoyl urea compound with one or more of the low-melting or liquid herbicides would offer an efficient and effective means of controlling a broad spectrum of grass and broadleaf weeds and sedges in cereal crop production. However, the sulfamoyl urea compound demonstrates unstable properties in the presence of certain low-melting or liquid herbicides and thereby loses efficacy and greatly reduces the potential control of broadleaf weeds and sedges. By low-melting herbicides, it is meant an herbicidal compound with a melting point of 60° C. or less.

Surprisingly, it has been found that an herbicidal combination composition comprising the sulfamoyl urea compound in combination with one or more low-melting or liquid herbicides in the presence of alkaline white carbon demonstrates excellent stability, effective broad spectrum weed control and desirable physical properties even after standing for long periods of time. Alkaline white carbon designates silicon dioxide ($SiO_2$) sorbtive carriers with a pH of about 9–12, preferably about 10–11. Among the alkaline white carbon products suitable for use in the composition of the invention are Carplex #100 or Carplex #1120 (manufactured by Shionogi Pharmaceutical Co.), Toksil AL-1 (manufactured by Tokuyama Soda Co.), Nipsil NA (manufactured by Nippon Silica Kogyo Co.) and the like, preferably Carplex #100 or Carplex #1120.

The Carplex white carbons comprise amorphous hydrous silicon dioxide synthesized by the wet process and are generally known as a type of precipitated silica. The Carplex white carbons are formed by agglomerate structuring from globular basic particles of about 20 to 30 mµ. Further description of the characteristics and properties of the Carplex white carbon including Carplex #100 and Carplex #1120, is available from the trade brochure entitled "CARPLEX® SHIONOGI, Amorphous hydrous silicon dioxide ($SiO_2.n\ H_2O$)" by Shionogi & Co., Ltd., Japan, which is incorporated herein by reference.

In one embodiment of the invention, the stable herbicidal combination composition may contain about 0.05– 25.0% by weight of the sulfamoyl urea compound, preferably about 0.05–5.0%, about 1–65% by weight of a low-melting or liquid herbicide and about 2–30% by weight of alkaline white carbon.

In actual practice, the composition of the invention may be formulated in any of the conventional dry forms such as dusts, dust concentrates, wettable powders, fine granulars, granulars, water dispersable granulars and the like utilizing agronomically acceptable adjuvants including carriers, surfactants, binders and the like.

Among the carriers suitable for use in these formulations are clay, talc, diatomaceous earth, bentonite, calcium carbonate, and the like. Conventional surfactants which may be used in the above formulations are non-ionic surfactants such as polyoxyethylene alkylaryl ether, polyoxyethylene styrylphenyl ether, polyoxyethylene sorbitan fatty acid ester and the like, and ionic surfactants such as alkylsulfate, alkylarylsulfonate, alkylsulfate ester, ligninsulfonate, alkylnapthalene sulfonate formalin condensate, sulfate of polyoxyethylene alkylaryl ether, alkylamine salt, dialkylsulfosuccinate, polycarbonate and the like. Binders such as carboxymethylcellulose may be used to improve the hardness of granule formulations.

For a more clear understanding of the invention, specific examples thereof are set forth below. These examples are merely illustrative and are not to be understood as limiting the scope and underlying principles of the invention in any way.

EXAMPLE 1

Preparation of Granular Combination Compositions With 1 -{[o-(cyclopropylcarbonyl)-phenyl]sulfamoyl}-3-(4,6 -dimethoxy-2-pyrimidinyl)urea And A Liquid Herbicide The liquid herbicide used in this example is esprocarb, a thiocarbamate herbicide.

The title sulfamoyl urea compound is pulverized and blended with either white carbon or alkaline white carbon. This blend is then mixed with clay or talc or $CaCO_3$, bentonite and surfactants. The resultant mixture is blended, kneaded with water and extruded through a 0.7–15 mm mesh screen. The resultant granules are dried, cut and sprayed with the liquid herbicide (esprocarb).

Using the above procedure, the following granular compositions are obtained and shown in Table I.

TABLE I

| INGREDIENT | wt/wt % | | | | | |
|---|---|---|---|---|---|---|
| | A | B | C | D | E | F |
| Sulfamoyl urea (91.9% pure) | 0.67 | 0.67 | 0.67 | 0.67 | 0.67 | 0.67 |
| Esprocarb (94.3% pure) | 22.94 | 22.94 | 22.94 | 22.94 | 22.94 | 22.94 |
| White Carbon[1] (ph 5.5–6.3) | 15.0 | 1.03 | 1.03 | 0.83 | — | — |
| White Carbon[2] (ph 7.0–8.0) | — | 17.5 | — | — | — | — |
| Alkaline White Carbon[3] (pH 10.1–10.6) | — | — | 17.5 | 17.5 | 17.5 | 17.5 |
| Clay | 28.93 | 18.86 | 18.86 | — | — | — |
| $CaCO_3$ | — | — | — | 20.06 | — | — |
| Talc | — | — | — | — | 26.09 | 22.89 |
| Bentonite - Na | 25.00 | 30.00 | 30.00 | 30.00 | 30.00 | 30.00 |
| Polycarbonate[4] | 3.00 | 3.00 | 3.00 | 3.00 | — | 3.00 |
| Dialkyl sulfosuccinate[5] | 3.00 | 3.00 | 3.00 | 3.00 | 0.8 | 3.00 |
| Styrenated phenol sulfate/ alkylbenzene sulfonate[6] | 2.00 | 2.00 | 2.00 | 2.00 | — | — |
| Epoxylated soybean oil[7] | — | 1.00 | 1.00 | — | — | — |
| Carboxymethylcellulose - Na[8] | — | — | — | — | 2.0 | — |

[1]Carplex #80 (Shionogi Pharmaceutical Co.)
[2]Carplex #67 (shionogi Pharmaceutical Co.)
[3]Carplex #100 (Shionogi Pharmaceutical Co.)
[4]Shallol AN103P (Dai-ichi Kogyo Seiyaku Co., Ltd.)
[5]Neocol YSK (Dai-ichi Kogyo Seiyako Co., Ltd.)
[6]New Kalgen TG-74 (Takemoto Oil & Fat Co., Ltd.)
[7]New Kalgen 800 (Takemoto Oil & Fat Co., Ltd.)
[8]Cellogen 7A (Dai-ichi Kogyo Seiyako Co., Ltd.)

EXAMPLE 2

Comparative Stability Evaluation Of Compositions Containing 1-{[ o-(cyclopropylcarbonyl)-phenyl]sulfamoyl}-3-(4,6 -dimethoxy-2-pyrimidinyl)urea And A Liquid Herbicide Test compositions prepared in Example 1 are placed in a screw-capped glass sample bottle and stored in a constant temperature oven set at 40° C. The samples are analyzed for active ingredient content after 0, 1, 2 and 3 month periods. Analyses are performed by reverse phase high speed liquid chromatography.

The percent recovery of the sulfamoyl urea compound is calculated using the equation shown below.

$$\% \text{ Recovery} = \frac{\text{Storage quantity}}{\text{Initial quantity}} \times 100$$

The results are shown in Table II.

TABLE II

Evaluation Of The Stability Of The Sulfamoyl Urea In A Combination Composition With A Liquid Herbicide And Alkaline White Carbon

| Test Sample | White Carbon | pH | Storage at 40° C. | | | | |
|---|---|---|---|---|---|---|---|
| | | | Initial Quantity[1] | 2 month Quantity[1] | 2 month % Recovery[1] | 3 month Quantity[1] | 3 month % Recovery[1] |
| IA | Carplex #80 | 5.5–6.3 | 0.58 | 0.28 | 48.3 | 0.16 | 32.8 |
| IB | Carplex #67 | 7.0–8.0 | 0.59 | 0.49 | 83.0 | 0.29 | 49.2 |
| IC | Carplex #100 | 10.1–10.6 | 0.53 | 0.55 | 100 | 0.33 | 62.3 |
| ID | Carplex #100 | 10.1–10.6 | 0.58 | 0.64 | 100 | 0.52 | 89.7 |
| IE | Carplex #100 | 10.1–10.6 | 0.58 | 0.55 | 94.8 | 0.43 | 74.1 |
| IF | Carplex #100 | 10.1–10.6 | 0.63 | 0.54 | 85.7 | 0.53 | 84.1 |

[1]Sulfamoyl urea compound

EXAMPLE 3

Preparation of Granular Combination Compositions Containing 1-{[o-(cyclopropylcarbonyl)-phenyl]sulfamoyl}-3-(4,6-dimethoxy-2-pyrimidinyl)urea And A Low-melting Herbicide The low-melting herbicide used in this example is pendimethalin, a dinitroaniline herbicide.

The sulfamoyl urea compound is mixed with a portion of the alkaline white carbon. Pendimethalin is melted using a water bath and blended with the remaining alkaline white carbon. The two mixtures are blended together and the remaining ingredients are added. The resultant mixture is blended, kneaded with water and extruded through an 0.7–15 mm mesh screen. The resultant granules are dried and cut.

Using the above procedure, the compositions shown on Table III are prepared.

TABLE III

| INGREDIENTS | % Wt/Wt | |
|---|---|---|
| | A | B |
| Sulfamoyl urea (91.9% pure) | 0.67 | 0.67 |
| Pendimethalin (91.8% pure) | 5.76 | 5.76 |
| Alkaline White Carbon[1] (pH 10.1–10.6) | 5.98 | 5.98 |
| Clay | — | 41.59 |
| Talc | 41.59 | — |
| Bentonite - Na | 40.0 | 40.0 |
| Polycarbonate type anionics[2] | 3.0 | 3.0 |
| Dialkylsulfosuccinate[3] | 3.0 | 3.0 |

[1]Carplex #100 (Shionogi Pharmaceutical Co.)
[2]Shallol AN103P (Dai-ichi Kogyo Seiyaku Co., Ltd.)
[3]Neocol YSK (Dai-ichi Kogyo Seiyaku Co., Ltd.)

EXAMPLE 4

Stability Evaluation Of Compositions Containing 1-{[o-(cyclopropylcarbonyl)-phenyl]sulfamoyl}-3-(4,6-dimethoxy-2-pyrimidinyl)urea And A Low-Melting Herbicide Test compositions prepared in Example 3 are placed in a screw-capped glass sample bottle and stored in a constant temperature oven set at 40° C. The samples are analyzed for active ingredient content after 0, 1, 2 and 3 month periods. Analyses are performed by reverse phase high speed liquid chromatography. The percent recovery of the sulfamoyl urea compound is calculated as described in Example 2. The data are shown below in Table IV.

TABLE IV

Evaluation Of The Stability Of The Sulfamoyl Urea In A Combination Composition With A Low-melting Herbicide And Alkaline White Carbon

| Test Sample | White Carbon | pH | Storage at 40° C. | | | | |
|---|---|---|---|---|---|---|---|
| | | | Initial Quantity | 2 month Quantity | 2 month % Recovery | 3 month Quantity | 3 month % Recovery |
| IIIA | Carplex #100 | 10.1–10.6 | 0.415 | 0.435 | 100 | 0.443 | 100 |
| IIIB | Carplex #100 | 10.1–10.6 | 0.428 | 0.422 | 98.6 | 0.394 | 92.0 |

EXAMPLE 5

Stability of a Granular Combination Composition Containing 1-{[0-(cyclopropylcarbonyl)-phenyl]sulfamoyl}-3-(4,6-dimethoxy-2-pyrimidinyl)urea And A Low-melting Herbicide The low-melting herbicide used in this example is pendimethalin, a dinitroaniline herbicide.

The compositions shown in Table V are prepared using the procedure set forth in Example 3.

The stability evaluation is conducted using the procedure outlined in Example 4, except that the test temperature is 55° C. and the sample analyses are conducted after one, two and four week periods. The data are shown below in Table V.

TABLE V

Evaluation of the Stability of the Sulfamoyl Urea in a Combination Composition with a Low-melting Herbicide and Alkaline White Carbon.

| | wt/wt % | | | | | |
|---|---|---|---|---|---|---|
| | VA | VB | VC | VD | VE | VF |
| Composition: | | | | | | |
| Sulfamoyl Urea | 0.6 | 0.6 | 0.6 | 0.6 | 0.6 | 0.6 |
| Pendimethalin | 5.0 | 5.0 | 5.0 | 5.0 | 5.0 | 5.0 |
| Carplex #80 | 6.0 | 6.0 | (—) | (—) | (—) | (—) |
| Carplex #67 | (—) | (—) | 6.0 | 6.0 | (—) | (—) |
| Carplex #100 | (—) | (—) | (—) | (—) | 6.0 | 6.0 |
| Clay | (—) | 41.6 | (—) | 41.6 | (—) | 41.6 |
| Talc | 41.6 | (—) | 41.6 | (—) | 41.6 | (—) |
| Bentonite-Na | 40.0 | 40.0 | 40.0 | 40.0 | 40.0 | 40.0 |
| Stability: | | | | | | |
| Initial | 0.517 | 0.553 | 0.534 | 0.534 | 0.497 | 0.500 |
| 55° C., 1 Week | 0.440 | 0.454 | 0.505 | 0.433 | 0.504 | 0.512 |
| 55° C., 2 Weeks | 0.358 | 0.352 | 0.469 | 0.337 | 0.472 | 0.472 |
| 55° C., 4 Weeks | 0.357 | 0.327 | 0.449 | 0.294 | 0.482 | 0.419 |
| (Recovery %) | (69.1) | (61.4) | (84.1) | (55.1) | (97.0) | (83.8) |

EXAMPLE 6

Stability of a Granular Combination Composition Containing 1-{[0-(cyclopropylcarbonyl)-phenyl]-sulfamoyl}-3-(4,6-dimethoxy-2-pyrimidinyl)urea And A Liquid Herbicide The liquid herbicide used in this example is molinate, a thiocarbamate herbicide.

The compositions shown in Table VI are prepared using the procedure set forth in Example 1.

The stability evaluation is conducted using the procedure outlined in Example 2, except that the test temperature is 55° C. and the sample analyses are conducted after two week and four week periods. The data are shown below in Table VI.

TABLE VI

Evaluation Of The Stability Of The Sulfamoyl Urea In A Combination Composition With A Liquid Herbicide And Alkaline White Carbon

| | wt/wt % | | | | | |
|---|---|---|---|---|---|---|
| | VIA | VIB | VIC | VID | VIE | VIF |
| Composition: | | | | | | |
| Sulfamoyl Urea[1] | 0.22 | 0.22 | 0.22 | 0.22 | 0.22 | 0.22 |
| Molinate[2] | 8.40 | 8.40 | 8.40 | 8.40 | 8.40 | 8.40 |
| Carplex #80 | 4.28 | 4.28 | 4.28 | (—) | (—) | (—) |
| Carplex #100 | (—) | (—) | (—) | 4.28 | 4.28 | 4.28 |
| Clay | 45.1 | (—) | (—) | 45.1 | (—) | (—) |
| Talc | (—) | 45.1 | (—) | (—) | 45.1 | (—) |
| CaCO₃ | (—) | (—) | 45.1 | (—) | (—) | 45.1 |
| Bentonite-Na | 40.0 | 40.0 | 40.0 | 40.0 | 40.0 | 40.0 |
| Neocol YSK[3] | 1.0 | 1.0 | 1.0 | 1.0 | 1.0 | 1.0 |
| Shallol AN103P[4] | 1.0 | 1.0 | 1.0 | 1.0 | 1.0 | 1.0 |
| Stability: | | | | | | |
| Initial | 0.183 | 0.168 | 0.149 | 0.129 | 0.122 | 0.138 |
| 55° C., 2 Weeks | 0.172 | 0.157 | 0.136 | 0.121 | 0.111 | 0.126 |
| 55° C., 4 Weeks | 0.093 | 0.072 | 0.009 | 0.115 | 0.092 | 0.073 |
| (Recovery %) | (50.8) | (42.9) | (6.0) | (89.1) | (75.4) | (52.9) |

[1]95.3% Pure
[2]97.6% Pure
[3]Neocol YSK (Dai-ichi Kogyo Seiyaku Co., Ltd.)
[4]Shallol AN103P (Dai-ichi Kogyo Seiyaku Co., Ltd.)

EXAMPLE 7

Stability of a Granular Combination Composition Containing 1-{[0-(cyclopropylcarbonyl)-phenyl]-sulfamoyl}-3-(4,6-dimethoxy-2-pyrimidinyl)urea And A Liquid Herbicide The liquid herbicide used in this example is butachlor, a chloroacetamide herbicide.

The compositions shown in Table VII are prepared using the procedure set forth in Example 1.

The stability evaluation is conducted using the procedure outlined in Example 6. The data are shown below in Table VII.

TABLE VII

Evaluation Of The Stability Of The Sulfamoyl Urea In A Combination Composition With A Liquid Herbicide And Alkaline White Carbon

| | wt/wt % | | | | | |
|---|---|---|---|---|---|---|
| | VIIA | VIIB | VIIC | VIID | VIIE | VIIF |
| Composition: | | | | | | |
| Sulfamoyl Urea[1] | 0.66 | 0.66 | 0.66 | 0.66 | 0.66 | 0.66 |
| Butachlor[2] | 8.33 | 8.33 | 8.33 | 8.33 | 8.33 | 8.33 |
| Carplex #80 | 5.01 | 5.01 | 5.01 | (—) | (—) | (—) |
| Carplex #100 | (—) | (—) | (—) | 5.01 | 5.01 | 5.01 |
| Clay | 41.0 | (—) | (—) | 41.0 | (—) | (—) |
| Talc | (—) | 41.0 | (—) | (—) | 41.0 | (—) |
| CaCO$_3$ | (—) | (—) | 41.0 | (—) | (—) | 41.0 |
| Bentonite-Na | 40.0 | 40.0 | 40.0 | 40.0 | 40.0 | 40.0 |
| Neocol YSK | 2.0 | 2.0 | 2.0 | 2.0 | 2.0 | 2.0 |
| Shallol AN103P | 3.0 | 3.0 | 3.0 | 3.0 | 3.0 | 3.0 |
| Stability: | | | | | | |
| Initial | 0.549 | 0.542 | 0.558 | 0.549 | 0.542 | 0.535 |
| 55° C., 2 Weeks | 0.481 | 0.494 | 0.496 | 0.490 | 0.492 | 0.504 |
| 55° C., 4 Weeks | 0.452 | 0.446 | 0.462 | 0.444 | 0.467 | 0.464 |
| (Recovery %) | (37.3) | (77.6) | (82.8) | (80.9) | (86.2) | (86.7) |

[1] 95.3% Pure
[2] >90% Pure

EXAMPLE VIII

Preparation Of Granular Combination Compositions With 1-{[o-(cyclopropylcarbonyl)-phenol] sulfamoyl}-3-(4,6-dimethoxy-2-pyrimidinyl)urea And A Low-Melting Solid Or A Liquid Herbicide Using the procedures described in Examples I and III, the following low-melting or liquid herbicides may be used in combination with the title sulfamoyl urea to prepare a stable herbicidal composition.

| Herbicide | mp °C. |
|---|---|
| Trifluralin | 48.5°–49° |
| Thiobencarb | 3.3° |
| Pretilachlor | liquid |
| Alachlor | 39.5°–41.5° |
| Metolachlor | liquid |

What is claimed:

1. A stable herbicidal composition which comprises a sulfamoyl urea compound, 1-{ [o-(cyclopropylcarbonyl)-phenyl] sulfamoyl} -3-(4,6-dimethoxy-2-pyrimidinyl)urea, one or more low-melting or liquid herbicides which produce unstable properties of the sulfamoyl urea compound and alkaline white carbon.

2. The composition according to claim 1 wherein the low-melting or liquid herbicide is selected from the group consisting of a dinitroaniline herbicide, a thiocarbamate herbicide and a chloroacetamide herbicide.

3. The composition according to claim 1 wherein the alkaline white carbon has a pH of about 9 or higher.

4. The composition according to claim 2 wherein the alkaline white carbon has a pH of about 10–11.

5. The composition according to claim 4 which comprises on a weight basis about 0.05–25.0% of the sulfamoyl urea compound, about 1–65% of the low-melting or liquid herbicides, about 2–30% by weight of the alkaline white carbon and 0–90% of an agronomically acceptable adjuvant or mixture thereof.

6. The composition according to claim 5 which comprises about 0.5–5.0% of the sulfamoyl urea compound, about 5–30% of the low-melting or liquid herbicides, about 10–30% of the alkaline white carbon, and about 30–60% of an agronomically acceptable adjuvant or mixture thereof.

7. The composition according to claim 5 wherein the low-melting or liquid herbicide is a dinitroaniline herbicide.

8. The composition according to claim 5 wherein the low-melting or liquid herbicide is a thiocarbamate herbicide.

9. The composition according to claim 5 wherein the low-melting or liquid herbicide is a chloroacetamide herbicide.

10. The composition according to claim 7 wherein the dinitroaniline herbicide is pendimethalin or trifluralin.

11. The composition according to claim 10 wherein the dinitroaniline herbicide is pendimethalin.

12. The composition according to claim 8 wherein the thiocarbamate herbicide is selected from the group consisting of esprocarb, benthiocarb, and molinate.

13. The composition according to claim 12 wherein the thiocarbamate herbicide is esprocarb.

14. The composition according to claim 12 wherein the thiocarbamate herbicide is molinate.

15. The composition according to claim 9 wherein the chloroacetamide herbicide is selected from the group consisting of butachlor, pretilachlor, metolachlor and alachlor.

16. The composition according to claim 15 wherein the chloroacetmide herbicide is butachlor.

17. The composition according to claim 5 wherein the alkaline white carbon is selected from the group consisting of Carplex #100 and Carplex #1120.

18. The composition according to claim 5 wherein the alkaline white carbon is an amorphous hydrous silicon dioxide.

19. A method for stabilizing an unstable mixture comprising a sulfamoyl urea compound, 1-{ [o-(cyclopropylcarbonyl)-phenyl]] sulfamoyl} -3-(4,6-dimethoxy-2 -pyrimidinyl)urea and one or more low-melting or liquid herbicides which produce unstable properties of the sulfamoyl urea compound, which comprises incorporating a stabilizing amount of an alkaline white carbon into the unstable mixture.

20. The method according to claim 19 wherein the alkaline white carbon has a pH of about 10–11.

21. A stable herbicidal composition which comprises a sulfamoyl urea compound, 1-{[-o-(cyclopropylcarbonyl)-phenyl]sulfamoyl}-3-(4,6-dimethoxy-2-pyrimidinyl)urea, one or more low-melting or liquid herbicides selected from the group consisting of esprocarb, molinate, pendimethalin and butachlor, and alkaline white carbon.

22. The composition according to claim 21 wherein the alkaline white carbon has a pH of about 9 or higher.

23. The composition according to claim 22 which comprises on a weight basis about 0.05–25.0% of the sulfamoyl urea compound, about 1–65% of the low-melting or liquid herbicides, about 2–30% by weight of the alkaline white carbon and 0–90% of an agronomically acceptable adjuvant or mixture thereof.

24. The composition according to claim 23 wherein the alkaline white carbon is selected from the group consisting of Carplex #100 and Carplex #1120.

* * * * *